United States Patent [19]
Mynarcik et al.

[11] Patent Number: 5,011,964
[45] Date of Patent: Apr. 30, 1991

[54] NOVEL DIACYLGLYCEROPHOSPHORIC ACID ESTERS AND USE THEREOF AS SUBSTRATES IN ENZYME ASSAYS

[75] Inventors: Dennis C. Mynarcik; Owen W. Griffith, both of New York, N.Y.; Gordon F. Fairclough, Jr., Norwalk, Conn.

[73] Assignee: Cornell Research Foundation, Inc., Ithaca, N.Y.

[21] Appl. No.: 505,695

[22] Filed: Apr. 6, 1990

[51] Int. Cl.$^5$ .......................... C07F 9/02; C07F 9/10; C12Q 1/42
[52] U.S. Cl. .................................. 558/179; 549/216; 549/220; 260/403; 435/21
[58] Field of Search .................. 558/179, 216, 220; 260/403

[56] References Cited

U.S. PATENT DOCUMENTS

| | | | |
|---|---|---|---|
| Re. 30,748 | 9/1981 | Sears | 260/403 |
| 3,875,013 | 4/1975 | Manauton et al. | 435/18 |
| 3,960,905 | 6/1976 | Eibl et al. | 260/403 |
| 4,039,388 | 8/1977 | Gal et al. | 435/21 |
| 4,041,111 | 8/1977 | Kelly et al. | 260/954 |
| 4,102,747 | 7/1978 | Driscoll | 435/22 |
| 4,129,650 | 12/1978 | Betzing et al. | 514/114 |
| 4,145,527 | 3/1979 | Burns | 536/17.8 |
| 4,147,860 | 4/1979 | Farnham | 536/17.8 |
| 4,225,672 | 9/1980 | Hall | 435/74 |
| 4,233,403 | 11/1980 | Menson et al. | 435/22 |
| 4,263,286 | 4/1981 | Nakajima et al. | 514/78 |
| 4,316,730 | 2/1982 | Eibl | 260/403 X |
| 4,348,329 | 9/1982 | Chapman | 260/403 |
| 4,426,330 | 1/1984 | Sears | 260/403 |
| 4,451,563 | 4/1984 | Kaufman | 435/21 |
| 4,472,499 | 9/1984 | McCroskey | 435/21 |

OTHER PUBLICATIONS

Carman et al., Analytical Biochemistry 110, 73–76 (1981).
Dawson et al., Biochemistry Journal, 102, 76–86 (1967).
Imamura et al., Journal of Biochemistry, 83, 677–680 (1978).
Mynarcik et al., Federation Proceedings, Abstracts ASBC/AAI Annual Meeting, American Societies for Experimental Biology, vol. 43, No. 6, 1458, Abstract #243 (5/1/84).
Van Boeckel, C. A. A. et al., Tetrahedron, 37(21), 3751–3761 (1981).
Dixon, M. et al., Enzymes, Academic Press, pp. 199–204 (1964).
Stenish, J. Dictionary of Biochemistry, John Wiley & Sons, p. 237 (1975).
Stryer, L. Biochemistry, 2d Edition, W. H. Freeman and Co., p. 461 (1981).
Bahl, O. P., The Journal of Biological Chemistry, 245, No. 2, Issue of Jan. 25, 1970, pp. 299–304.
Aminoff, D. et al., The Journal of Biological Chemistry, 245, No. 7, Issue of Apr. 10, 1970, pp. 1659–1669.
Yurewicz, E. C. et al., The Journal of Biological Chemistry, 246, No. 18, Issue of Sep. 25, 1971, pp. 5607–5616.
Kozak, E. M. et al., The Journal of Biological Chemistry, 257, No. 11, Issue of Jun. 10, 1982, pp. 6322–6327.
Barman, T. E. *Enzyme Handbook*, vol. 1, pp. 521–524, 544, 545, 560–561, 576–579, Springer-Verlang, New York, Inc. 1969.
Hofmann, S. L. et al., *The Journal of Biological Chemistry* (1982), vol. 257, pp. 6461–6469.
Jencks, W. P., *Catalysis in Chemistry and Enzymology*, McGraw-Hill, 1969, pp. 60–65.
Yang, S. F. et al., *The Journal of Biological Chemistry*, (1967), vol. 242, pp. 477–484.
de Lumen, B. O. et al., The Journal of Biological Chemistry, 247, No. 11, Issue of Jun. 10, 1972, pp. 3552–3557.
Saito, M. et al., Archives of Biochemistry and Biophysics, 164, 420–428 (1974).
Enzyme Nomenclature, Academic Press, pp. 248, 250 (1978).
Calama, M. A. et al., Chemical Abstracts, 75: 1983 y (1971).
Boehringer Catalog, pp. 461 and 463.
Billah, M. M. et al., Journal of Biological Chemistry, 264 (69) 17069–17077 (1989).
Davitz, M. A., Science, 238, pp. 81–84 (10/87).
Kurioka, S. et al., Analytical Biochemistry 75, 281–289 (1976).

*Primary Examiner*—Cecilia Shen

[57] ABSTRACT

Novel diacylglycerophosphoric acid esters include a hydrophobic diacyl glycerol portion to provide water insolubility and a head group which forms a chromophore or a chromophore precursor when the head group is enzymatically released and are chromogenic substrates useful to assay for enzymes catalyzing the cleavage of phosphate ester or phosphoanhydride bonds adjacent or opposite to the phosphatidic acid region of a phospholipid molecule.

8 Claims, No Drawings

NOVEL DIACYLGLYCEROPHOSPHORIC ACID ESTERS AND USE THEREOF AS SUBSTRATES IN ENZYME ASSAYS

This is a continuation of copending application Ser. No. 06/709,256 filed on Mar. 7, 1985 now abandoned.

TECHNICAL FIELD

This invention relates to novel diacylglycerophosphoric acid esters and the use thereof as chromogenic substrates for phospholipase C, phospholipase D, and analogous enzyme activities.

BACKGROUND OF THE INVENTION

Phospholipase D characterizes a group of enzymes which transfer a phosphatidic acid moiety from an acid or an alcohol to an alcohol or water. The activity is found, for example, in vegetables, such as carrots and cabbage. The enzyme species found in cabbage is widely studied and has been denoted as phosphatidylcholine phosphatidohydrolase (Enzyme Commission No. 3.1.4.4). This enzyme hydrolyzes phosphatidylcholine into phosphatidic acid and choline. This enzyme has been assayed by using radiolabeled phosphatidylcholine or by using coupled enzyme assays which detect the product choline. These assays are complicated and/or difficult.

Phospholipase C characterizes a group of enzymes which transfer phosphate monoester from a donor alcohol to an acceptor alcohol or water, where diacylglycerol is either the donor or the acceptor group. A species of the enzyme is recognized to have important physiological significance in coupling a hormone binding event outside a cell whereby diacylglycerol is freed to transmit a signal to activate a metabolic response inside the cell. The phospholipase C activity of phosphatidylcholine cholinephosphohydrolase has been assayed using a p-nitrophenylphosphorylchcline (pNPPC) as a chromogenic substrate. The disadvantage of pNPPC is that its cleavage is not specific to lipases which have been defined as esterases which act at oil-water interfaces by P. Desnuelle in *Advances in Enzymology* (1961), Vol. 21, pp. 129–161.

SUMMARY OF THE INVENTION

It has been found herein that particular novel diacylglycerophosphoric acid esters function as chromogenic substrates for phospholipase D and phospholipase D-like enzymes and thus provide a simpler method for assaying these enzymes than is now available.

The novel diacylglycerophosphoric acid esters herein include a hydrophobic diacylglycerol portion to provide water insolubility and a head group to provide a chromophore or chromophore precursor when the head group is enzymatically released.

The novel diacylglycerophosphoric acid esters herein have the structural formula:

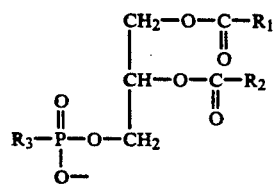

wherein $R_1$ and $R_2$ are organic groups where at least one of them or the combination of them causes the compound to be insoluble in water and $R_3$ is a chromogenic head group which forms a chromophore or chromophore precursor when released.

These novel compounds are useful for assaying phospholipase D or phospholipase D-like enzymes. The method of carrying out this assay comprises the steps of (a) admixing a sample to be assayed for such enzyme with an aqueous composition containing the diacylglycerophosphoric acid ester of this invention as a chromogenic substrate to obtain a selected concentration of said ester and establish conditions for chromophore or chromophore precursor release, (b) monitoring changes in light absorption or fluorescence in the admixture to provide data relating to the rate of chromophore or chromophore precursor release, and (c) correlating the rate of chromophore or chromophore precursor release to phospholipase D or phospholipase D-like enzyme activity.

The novel compounds herein are also useful for assaying for phospholipase C. The method of carrying out this assay comprises the steps of admixing sample to be assayed for phospholipase C activity with an aqueous composition containing the diacylglycerophosphoric acid ester of this invention as a chromogenic substrate and either acid or alkaline phosphatase as a supplementary enzyme to obtain selected concentrations of said ester and said supplementary enzyme and establish conditions for chromophore or chromophore precursor release, (b) monitoring changes in light absorption or fluorescence in the admixture to provide data relating to rate of chromopore or chromophore precursor release, and (c) correlating the rate of chromophore release or chromopore precursor release to phospholipase C activity.

As used herein the term substrate means a molecule that is acted on by an enzyme.

As used herein the term chromophore relates to a molecule that interacts with light to absorb radiation at a particular wavelength so that its concentration can be sensed spectrophotometrically or that emits radiation of a different wavelength subsequent to radiation absorption so that its concentration can be sensed spectrofluorometrically.

As used herein the term chromophore precursor relates to a molecule which reacts to form a chromophore, e.g. by diazotization.

As used herein the term chromogenic means capable of generating a chromophore or chromophore precursor on hydrolysis or alcoholysis.

As used herein, the term water insoluble means a solubility less than about 1 mmole per liter of water at a temperature of 25° C.

DETAILED DESCRIPTION OF THE INVENTION

Turning firstly to the diacylglycerophosphoric acid ester, the $R_1$ and $R_2$ groups can be the same or different but must be such that the combination of them is sufficiently hydrophobic so that the ester is water insoluble.

Preferably $R_1$ and $R_2$ are independently selected from the group consisting of aliphatic, aryl and alkylaryl groups, and when $R_1$ and $R_2$ are both aliphatic each contains from 1 to 23 carbon atoms and both together contain at least 8 carbon atoms. The alkyl in the alkylaryl group normally contains from 1 to 17 carbon atoms.

Turning more definitely to the case where $R_1$ and $R_2$ are both aliphatic, these each can be either saturated or unsaturated (containing for example up to 6 unsaturated sites). Very preferably $R_1$ and $R_2$ are each alkyl and are the same and each contains from 13 to 17 carbon atoms.

Very preferably $R_1$ and $R_2$ are each $C_{15}H_{31}$—, i.e.

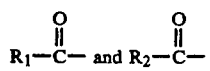

are each palmityl. In other highly preferred combinations,

are both myristyl or are both stearyl.

Other suitable combinations of

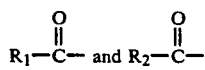

are as follows:

| | $R_1-C-$ ‖ O | $R_2-C-$ ‖ O |
|---|---|---|
| (a) | caprylyl | caprylyl |
| (b) | capryl | capryl |
| (c) | lauryl | lauryl |
| (d) | stearyl | oleyl |
| (e) | stearyl | linoleyl |
| (f) | stearyl | linolenyl |
| (g) | acetyl | arachidyl |
| (h) | acetyl | gadoleyl |
| (i) | arachidonyl | propionyl |
| (j) | behenyl | butyryl |
| (k) | erucyl | caproyl |
| (l) | oleyl | oleyl |
| (m) | acetyl | clupanodonyl |
| (n) | nisinyl | acetyl |
| (o) | valeryl | valeryl |

Other suitable combinations are as follows: $R_1$ is methyl and $R_2$ is phenyl; $R_1$ is anthracenyl and $R_2$ is methyl; $R_1$ is ethyl and $R_2$ is naphthyl; $R_1$ is pyrenyl and $R_2$ is methyl; both $R_1$ and $R_2$ are phenyl; $R_1$ is dodecylphenyl and $R_2$ is methyl; $R_1$ is hexylphenyl and $R_2$ is methyl; $R_2$ is octadecylphenyl and $R_1$ is methyl.

Turning now in detail to the $R_3$ group, suitable groups often contain (i.e. are or include) substituted phenol, naphthol, substituted naphthol or substituted umbelliferone moieties.

Suitable $R_3$'s which contain substituted phenol moieties include, for example, p-nitrophenol (i.e. 4-nitrophenol), 5-hydroxy-2-nitrobenzoic acid, 2-hydroxy-5-nitrobenzoic acid, N,N,N-trimethyl-N-(5-hydroxy-2-nitrophenyl)ammonium chloride, N,N,N-trimethyl-N-(2-hydroxy-5-nitrophenyl)ammonium chloride, 3-amino-4-nitrophenol, 2-amino-4-nitrophenol, 5-hydroxy-2-nitrobenzenesulfonic acid, and 2-hydroxy-5-nitrobenzenesulfonic acid.

Suitable $R_3$'s which contain naphthol or substituted naphthol moieties include, for example, α-naphthol (i.e. 1-naphthol), 4-amino-1-naphthol, 4-hydroxy-1-trimethylammoniumnaphthylene chloride, 4-hydroxy-1-naphthoic acid, 3-amino-1-naphthol, 4-hydroxy-2-trimethylammoniumnaphthylene chloride, 4-hydroxy-2-naphthoic acid, 8-amino-1-naphthol, 8-hydroxy-1-trimethylammoniumnaphthylene chloride, 8-hydroxy-1-naphthoic acid, 5-amino-1-naphthol, 5-hydroxy-1-trimethylammoniumnaphthalene chloride, 5-hydroxy-1-naphthoic acid, and 2-nitro-1-naphthol.

Suitable $R_3$'s which contain substituted umbelliferone moieties include, for example, 4-methylumbelliferone, 3-amino-4-methylumbelliferone, 3-trimethylammonium-4-methylumbelliferone chloride, 4-methyl-5-aminoumbelliferone, 4-methyl-6-aminoumbelliferone, 5-trimethylammonium-4-methylumbelliferone chloride, 6-trimethylammonium-4-methylumbelliferone chloride, 4-methylumbelliferone-5-sulfonic acid, 4-methylumbelliferone-6-sulfonic acid, 3-trimethylammonium-4-methylumbelliferone-5-sulfonate, 3-trimethylammonium-4-methylumbelliferone-5-carboxylic acid chloride, and 3-trimethylammonium-4-methylumbelliferone chloride.

Preferably $R_3$ is p-nitrophenol or α-naphthol or 4-methyl-umbelliferone.

The $R_3$'s which contain naphthol ordinarily form chromophore precursors following enzymatic cleavage and are used in conjunction with diazotizing reagents to form chromophores.

The most preferred ester herein is a phosphatidyl-p-nitrophenol and particularly is 1,2-dipalmitoyl phosphatidyl-p-nitrophenol (herein after PpNP). The hydrolysis product of this, that is p-nitrophenol, is at basic pH chromophoric at a wavelength (Y) of 404 nanometers where it has a molar absorptivity, that is extinction coefficient (e), of 18,750 at pH 10.3. This very preferred ester has the above recited structural formula wherein

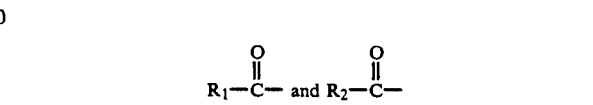

are palmityl and $R_3$ is p-nitrophenol.

Another preferred ester herein is a phosphatidyl-α-naphthol. Exemplary of this is 1,2-dipalmitoyl phosphatidyl-α-naphthol; this compound has the above cited structural formula wherein $R_1$ and $R_2$ are each $C_{15}H_{31}$—, i.e.

are each palmityl, and $R_3$ is α-naphthol. The hydrolysis product that is α-naphthol has the ability to be monitored continuously at acid pH following diazotization concurrent with enzymatic hydrolysis. Suitable diazotizing agents include, for example, Fast Red TR and p-diazobenzenesulfonic acid.

Another very suitable ester herein is a phosphatidyl-4-methylumbelliferone especially the 1,2-dipalmityl compound. This ester releases upon hydrolysis 4-methylumbelliferone. The 1,2-dipalmityl compound has the above recited structure wherein $R_1$ and $R_2$ are each $C_{15}H_{31}$—, i.e.

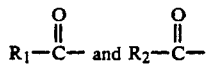

are each palmityl, and $R_3$ is 4-methylumbelliferone. The hydrolysis product that is 4-methylumbelliferone or 7-hydroxy-4-methylcoumarin is highly fluorescent at basic pH yielding an increase in sensitivity when the reaction is monitored spectrofluorometrically.

The wavelength used to spectrophotometrically quantitate the chromophore or diazotized chromophore precursor is determined empirically by taking the absorbance spectrum of the appropriate hydrolysis product in a suitable medium where its absorbance is maximally different from that of the chromogenic substrate. A similar approach is taken with the fluorescent hydrolysis products where the emission maximum and the absorption maximum are determined empirically with a spectrofluorometer. The quantitation of the chromophore or diazotized chromophore precursor is determined by comparison with standards measured under similar conditions. When appropriate molar absorptivities are calculated or obtained through the literature, they can be used for chromophore quantitation. Information on the wavelength of maximum absorption of specific diazotized chromophore precursors are available in *Synthetic Dyes in Biology, Medicine and Chemistry* by E. Gurr, 1971, Academic Press, and *A. J. Conn's Biological Stains*, 9th Ed. by R. D. Lillie, 1977, Williams and Wilkins Co.

The esters herein are readily prepared, for example, by reacting $R_3H$ with $POCl_3$ in a condensation reaction to form the corresponding phosphorodichloridate then condensing the phosphorodichloridate with 1,2-diglyceride, then hydrolyzing to form the phosphodiester and remove the remaining chlorine from phosphorous. Triethylamine or other buffering agent is preferably present during the last two steps to prevent accumulation of hydrogen chloride In some cases, the phosphorodichloridate formed in the first step may be available commercially so that that compound can be purchased and synthesis started at the second step. For example, p-nitrophenyl phosphorodichloridate used in the synthesis of PpNP is available commercially. The phosphorodichloridate utilized in synthesizing dipalmitoyl phosphatidyl-α-naphthol, PαN, is α-naphthol phosphorodichloridate and the phosphorodichloridate utilized in synthesizing dipalmityl phosphatidyl-4-methylumbelliferone, PMU, is 4-methylumbelliferonyl phosphorodichloridate.

A reaction equation for the synthesis for PpNP is set forth below

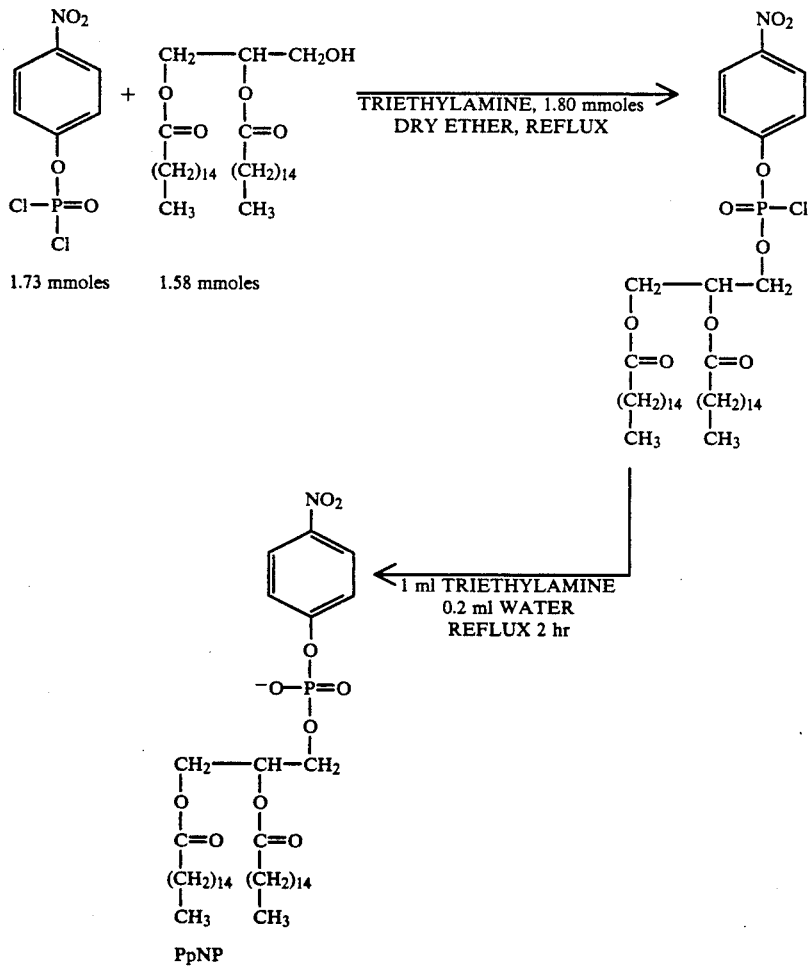

We turn now to the use of the esters herein for assaying enzymes.

The esters herein are chromogenic substrates useful for assaying enzymes which catalyze the hydrolysis or alcoholysis of the phosphate ester or phosphoanhydride bond opposite to the phosphatidic acid region of the phospholipid molecule, i.e. the bond between the phosphorus and the oxygen in the phosphate ester moiety which is not glyceride. These enzymes cleave between the phosphorus and the oxygen which is attached to the head group. These enzymes include phospholipase D and phospholipase D-like enzymes. As indicated above, one phospholipase D enzyme is derived from cabbage and known as phosphatidylcholine phosphatidohydrolase. Examples of phospholipase D-like enzymes are glycerolphosphate phosphatidyl transferase and inositol phosphatidyl transferase. Each enzyme has optimum conditions where it catalyzes cleavage and thus the assay can be made specific by selecting the optimum conditions for a particular enzyme. Conditions normally include an optimum pH, an optimum temperature and optimum emulsifying agents. For phosphatidylcholine phosphatidohydrolase when PpNP is utilized, hydrolysis is facilitated for example at a pH ranging from 5.6 to 6.5 and the optimum temperature is 40° C. and there is a preference for the presence of calcium and the surfactant/emulsifying agent used is preferably a zwitterionic detergent. While 40° C. is the optimum, temperatures in the range of 35° C. to 45° C. are readily utilized. Very suitable zwitterionic detergents include the N-alkyl-N,N-dimethyl-3-ammonio-1-propanesulfonates wherein the alkyl group contains from 8 to 16 carbon atoms; especially preferred is the compound wherein the alkyl group is tetradecyl, and such compound is sold under the name Zwittergent ® 3-14 by Calbiochem-Behring. Another suitable surfactant for use in analysis of the phospholipase D from cabbage using PpNP is the nonionic surfactant n-octyl-$\beta$-D-glucopyranoside. Thus, specific conditions of pH, temperature, emulsifying agent and other ions such as calcium ion are established to provide a hydrolytic rate such that hydrolysis is completed in a short period of time, for example 10 minutes, so that the assay is carried out in an effective period of time.

In analyzing for phospholipase D or phospholipase D-like enzymes, an aqueous mixture is made up containing the ester herein as well as other appropriate additives such as buffering agents, emulsifying agents and anything else that is required or preferred for the hydrolysis such as the calcium which is used for the cabbage-derived phospholipase D as explained above. These are added in the appropriate relative amounts. Then the temperature is adjusted to that within the preferred range, most preferably to the optimum temperature for the hydrolytic reaction. Then the sample suspected to contain the enzyme is admixed with the aforedescribed mixture in sufficient amount to obtain a standard selected concentration of chromogenic ester and other agents (emulsifying agent, $Ca^{++}$, etc.). At selected intervals of time after the admixing, for example, every 2 minutes over a 10 minute period, aliquots are removed and added to an aqueous solution containing agent to stop the reaction and clarify the mixture if there is a turbidity (for example, the solution used with the cabbage phospholipase D and PpNP contains 120 mM glycine, pH 10.4, to increase the pH, 20 mM ethylenediamine tetraacetic acid to chelate the calcium, both of which serve to stop the reaction, and 5 mM sodium dodecylsulfate, to clarify the turbidity). Each aliquot so treated is then read in the appropriate device, either a spectrophotometer or a spectrofluorometer, at the wavelength associated with the absorption maximum or the emission maximum of the chromophore released by enzymatic cleavage of the chromogenic substrate or of the azo dye formed by the diazotization of the chromophore precursor so released. Quantitation is achieved by comparison of the results with those obtained with known amounts of chromophore or, if the molar absorptivity coefficient is known, by application of Beer's Law, $A = \epsilon l c$, where A is the spectral absorbance, $\epsilon$ is the molar absorptivity coefficient, l is the path length of the cuvette, and c is the molar concentration of the chromophore. The number of moles of product formed as a function of time provides a rate of reaction which is proportional to the enzyme quantity. A unit of enzyme activity is defined as the amount of enzyme catalyzing the release of a selected amount of chromophore or chromophore precursor under the selected assay conditions per unit time.

The aforementioned method of removing aliquots is preferred when PpNP is used for the assay of cabbage derived phospholipase D since the enzymatic hydrolysis requires an acid pH and color formation which is read by the spectrophotometer requires a basic pH. In cases where the pH utilized for the hydrolysis is the same as that for color formation, continuous monitoring can be carried out. Where the ester herein is required to be utilized with a diazotizing agent, the diazotizing agent is included in the reaction mixture during assay for continuous monitoring or is added to aliquots which are removed at selected intervals of time.

The ester herein is also useful in the assay of enzymes which catalyze the hydrolysis of the phosphate ester bond adjacent to the diacylglycerol region of a phospholipid molecule, that is the bond between the phosphorus and the oxygen in the phosphate ester moiety which is glyceride. Such enzymes catalyze hydrolysis involving cleaving between the phosphorus and the oxygen which is attached to the glycerol backbone. This kind of activity is carried out by phospholipase C enzymes and as indicated above a specific species of phospholipase C is known as phosphatidylcholine cholinephosphohydrolase. The ester herein is utilized in combination with a supplementary enzyme which is either acid or alkaline phosphatase depending on the pH used for hydrolysis. The phospholipase C catalyzes hydrolysis of the substrate to release a diacylglycerol and a phosphate monoester. The supplementary enzyme hydrolyzes the phosphate monoester to release the head group which is chromophoric or a chromophore precursor. As with the phospholipase D enzymes, preferred conditions of temperature, for example 25 to 45° C., and pH, for example ranging from 5.5 to 10.5, are utilized so that reaction is carried out within a time framework consistent with expedient analysis, for example 5 to 15 minutes. Similarly, surfactant/emulsifier is selected to provide reaction within this time period. Any other agents which are necessary for activation of the enzyme are also included. The steps for carrying out the assay are the same as those used for assaying phospholipase D or phospholipase D-like enzymes except that the supplementary enzyme is included in the mixture containing the ester of the invention.

The standard concentrations of the ester of the invention which are utilized in the assays herein normally range from 0.1 to 50 mM and for PpNP normally range from 0.1 to 50 mM. The standard concentration of supplementary enzyme which is utilized normally ranges from about 0.1 to about 20U/ml. The activity of the supplementary enzyme is chosen to be 10 to 100 fold higher than the maximum amount of phospholipase C that may be present.

The following examples are illustrative of the invention.

EXAMPLE I

Synthesis of PpNP

PpNP was synthesized by reacting p-nitrophenyl-phosphorodichloridate with D(−)-1,2-dipalmitin as follows: To 20 ml of boiling, dry, diethylether, containing 1.8 mmoles of D(−)-1,2-dipalmitin, and 3.4 mmoles triethylamine, was added, dropwise with stirring, 7 ml of dry diethylether containing 2.3 mmoles of p-nitrophenylphosphorodichloridate. The disappearance of the D(−)-1,2-dipalmitin and the appearance of product was followed by TLC. When the D(−)-1,2-dipalmitin was maximally consumed, 1 ml of triethylamine and 0.2 ml of water were added to the reaction mixture which was then refluxed for 2 hours. The reaction mixture was then acidified with 10 ml of 1 N HCl and was then extracted three times with diethylether. The ether solution was then washed with water, dried over anhydrous $MgSO_4$, evaporated, and the residue dried further under vacuum over $P_2O_5$. PpNP was purified by preparative TLC on silica gel using chloroform-methanol-water (70:26:4).

The product of the synthetic reaction was a white powder weighing 1.405 g. The most abundant component of the crude powder migrated with an RF of 0.69 in the TLC system, using rhodamine 6-G for visualization under UV light. The band of $R_F$ of 0.69 comprised 64% of the crude product. It was isolated from the TLC plates and was demonstrated to be PpNP by its ratio of phosphate:p-nitrophenol:acyl group of 1.00:0.94:2.08.

EXAMPLE II

Selection Of Preferred Surfactant

A variety of surfactants were screened to determine a preferred surfactant for PpNP hydrolysis by phospholipase D (EC 3.1.4.4). In each case PpNP and surfactant were used in a mole ratio of 2:1. In each case, substrate mixture was prepared by adding the PpNP in a volatile solvent to a glass tube and evaporating the solvent under an $N_2$ stream. Then surfactant, sodium acetate buffer and water were added with mixing. The $CaCl_2$ was added. Then the enzyme was added. Then the mixture was incubated at 37° C. for 10 minutes at which point the reaction was stopped by adding a solution which raised the pH, chelated the calcium and cleared the turbidity as described previously. The conditions for enzyme reaction in each case were 0.1 M sodium acetate, pH 5.9, 50 mM $CaCl_2$, 37° C. Results obtained in terms of nanomoles (nmol) of head group released were as follows. In the following Z stands for N-alkyl-N,N-dimethyl-3-ammonio-1-propanesulfonate and the number following the Z stands for the number of carbon atoms in the alkyl group: sodium dodecylsulfate: 0.3 nmol; Z8: 3.3 nmol; Z10: 3.6 nmol; Z12: 7.9 nmol; Z14: 9.4 nmol; Z16: 8.6 nmol; n-octyl-β-D-glucopyranoside: 4.6 nmol. The data indicated that the preferred surfactant of those tried for PpNP hydrolysis by phospholipase D is N-tetradecyl-N,N-dimethyl-3-ammonio-1-propanesulfonate.

EXAMPLE III

Assay of Phospholipase D Using PpNP

Phospholipase D from cabbage was assayed using PpNP prepared as set forth in Example I as the substrate.

This assay is based on phospholipase D hydrolyzing PpNP at a rate which increases as a linear function of phospholipase D concentration under the conditions of 0.1 M sodium acetate (pH 5.9), 50 mM calcium chloride, 0.20 mM Zwittergent 3-14, 0.40 mM PpNP and phospholipase D at 37° C.

Assays were carried out on three samples of 0.10 units of phospholpse D contained in 0.1 ml of deionized water, on three samples of 0.25 units of phospholipase D contained in 0.1 ml of deionized water and on three samples of 0.5 units of phospholipase D contained in 0.1 ml of deionized water (the activities being those defined by the supplier Sigma Chemical Co. of St. Louis, Mo.).

The substrate mixture was prepared by dispensing into a 13×100 mm clean glass tube 0.522 ml of PpNP, 4.6 mM in chloroform ($2.4 \times 10^{-6}$ mole PpNP). The chloroform was evaporated under a stream of nitrogen. The solvent free PpNP was then reconstituted by adding 0.102 ml of Zwittergent 3-14 stock solution (10 mM in water, $1.02 \times 10^{-6}$ mole Zwittergent 3-14) and 3.778 ml of deionized water followed by heating to 50° C. and mixing on a vortex mixer until a suspension of homogeneous appearance was obtained. Into each of nine 1.5 ml screw-cap polypropylene microtubes appropriately labeled as to enzyme quantity (0.1, 0.25 or 0.5 units) and which replicate (a, b or c) was dispensed 0.420 ml of the prepared substrate suspension. (These tubes will be called the assay tubes). This was followed by the addition of 65 μl of 1.0 M sodium acetate (pH 5.9) to each of the nine tubes which were then capped and mixed on a vortex mixer. To facilitate the mechanics of the assay, the assays of the three different amounts of phospholipase D were carried out at three consecutive fifteen minute intervals. A set of test tubes were labeled so as to indicate which enzyme amount (0.10, 0.25 or 0.50 units), which replicate (a, b or c), and which time point within the assay (0, 2, 4, 6, 8 or 10 min.), fifty four tubes in all. (These tubes are referred to as the quench tubes). To each of these tubes was added 0.90 ml of the quenching solution which consisted of 120 mM glycine (pH 10.4), 20 mM ethylenediaminetetraacetic acid and 5 mM sodium dodecylsulfate. Prior to the addition of the phospholipase D the substrate was preincubated for sixty minutes with calcium at 37° C. as follows: A stopwatch was used to keep track of time during the assay. At 00:00, 00:40 and 01:20 65 μl of 0.5 M calcium chloride solution was added to the assay tubes labeled 0.1 a, 0.1 b and 0.1 c respectively. Following each addition, the assay tube was capped, vortexed and placed in a 37° C. water bath for the sixty minute preincubation period. This procedure was subsequently carried out at 15:00, 15:40, 16:20, 30:00, 30:40 and 31:20 on the assay tubes labeled 0.25 a, 0.25 b and 0.25 c, 0.5 a, 0.5 b and 0.5 c respectively. At the end of the sixty minute preincubation period the appropriate enzyme solution was added to the properly labeled assay tube as a 0.10 ml aliquot. This brought the final volume to 0.650 ml and the concentrations of the constituents to 0.40 mM for PpNP, 0.17 mM for Zwittergent 3-14, 0.1 M for sodium acetate and mM for calcium chloride. The enzyme solutions were maintained on ice and were brought to 37° C.

immediately prior to use (0.1 U/0.1 ml at sixty minutes, 0.25 U/0.1 ml at seventy five minutes and 0.5 U/0.1 ml at ninety minutes). A one hundred microliter automatic pipettor using disposable tips was used to carry out all of the pipetting operations of the assay. The spectrophotometric readings were made using a Cary 210 spectrophotometer at 404 nm in 1 cm quartz cuvettes. The data are displayed in Table I.

TABLE I

| ENZYME | TIME | a | b | c |
|---|---|---|---|---|
| 0.10 unit | 0 | 0.0074 | 0.0069 | 0.0072 |
| | 2 | 0.0095 | 0.0091 | 0.0096 |
| | 4 | 0.0106 | 0.0111 | 0.0114 |
| | 6 | 0.0157 | 0.0145 | 0.0169 |
| | 8 | 0.0167 | 0.0166 | 0.0166 |
| | 10 | 0.0202 | 0.0209 | 0.0184 |
| 0.25 unit | 0 | 0.0086 | 0.0079 | 0.0079 |
| | 2 | 0.0134 | 0.0133 | 0.0142 |
| | 4 | 0.0191 | 0.0174 | 0.0183 |
| | 6 | 0.0250 | 0.0149 | 0.0183 |
| | 8 | 0.0304 | 0.0283 | 0.0290 |
| | 10 | 0.0365 | 0.0348 | 0.0349 |
| 0.5 unit | 0 | 0.0101 | 0.0094 | 0.0096 |
| | 2 | 0.0206 | 0.0195 | 0.0187 |
| | 4 | 0.0321 | 0.0284 | 0.0276 |
| | 6 | 0.0423 | 0.0389 | 0.0382 |
| | 8 | 0.0506 | 0.0451 | — |
| | 10 | 0.0576 | 0.0520 | — |

The amount of p-nitrophenol released during the timed interval was determined using Beer's Law, $A = \epsilon l c$ where A is the absorbance at 404 nm, e is the molar absorptivity coefficient of p-nitrophenol in the quench medium (18750 $M^{-1}cm^{-1}$), l is the path length of the cuvette (1 cm) and c is the concentration of p-nitrophenol in moles per liter. the amount of p-nitrophenol released during each interval was calculated using the equation:

$$\text{Total moles released} = (A_{404} \times 18750)(6.5 \times 10^{-3}).$$

The total number of moles of p-nitrophenol released during the timed intervals and the mean of all the replicates are in Table II, the data are in nanomoles ($10^{-9}$ moles).

TABLE II

| ENZYME | TIME | a | b | c | MEAN |
|---|---|---|---|---|---|
| 0.1 unit | 0 | 2.57 | 2.39 | 2.50 | 2.49 |
| | 2 | 3.29 | 3.16 | 3.33 | 3.26 |
| | 4 | 3.68 | 3.85 | 3.95 | 3.83 |
| | 6 | 5.44 | 5.03 | 5.86 | 5.44 |
| | 8 | 5.79 | 5.76 | 5.76 | 5.77 |
| | 10 | 7.00 | 7.25 | 6.38 | 6.87 |
| 0.25 unit | 0 | 2.98 | 2.74 | 2.74 | 2.82 |
| | 2 | 4.65 | 4.61 | 4.92 | 4.73 |
| | 4 | 6.62 | 4.03 | 6.34 | 6.33 |
| | 6 | 8.94 | 8.63 | 8.84 | 8.80 |
| | 8 | 10.54 | 9.81 | 10.05 | 10.13 |
| | 10 | 12.65 | 12.06 | 12.10 | 12.27 |
| 0.5 unit | 0 | 3.50 | 3.26 | 3.33 | 3.36 |
| | 2 | 7.14 | 6.76 | 6.48 | 6.79 |
| | 4 | 11.13 | 9.85 | 9.57 | 10.18 |
| | 6 | 14.66 | 13.49 | 13.24 | 13.80 |
| | 8 | 17.54 | 15.63 | — | |
| | 10 | 19.97 | 18.03 | — | |

The rate of PpNP hydrolysis was determined using the linear regression analysis program of a Hewlett Packard 10 C calculator and that data is listed in Table III where the slope is the rate in $10^{-9}$ moles min $^{-1}$ and the correlation coefficient (r) is a measure of the relative agreement of the data with a linear function where 1.0000 is a perfect correlation.

TABLE III

| ENZYME | SLOPE | r |
|---|---|---|
| 0.1 unit | 0.44 | 0.9892 |
| 0.25 unit | 0.94 | 0.9982 |
| 0.5 unit | 1.74 | 0.9999 |

Applying linear regression analysis to the data in Table III yields the rate of PpNP hydrolysis per unit of activity of cabbage phospholipase D. The slope is 3.25 nanomoles per minute per unit of phospholipase D from cabbage as assessed by the supplier with a correlation coefficient of 0.9999.

Thus, the data shows that in assaying an unknown under the assay conditions set forth in this Example, the amount of activity in terms of the supplier's units is determined by dividing the rate of hydrolysis in nanomoles per minute by 3.25 nanomoles per minute/units.

Example IV

Assay of Phospholipase C Using PpNP and Supplementing Enzyme

The assay is performed as in Example III with the following exceptions.

The substrate mixture is prepared by reconstituting $9 \times 10^{-6}$ moles of solvent free PpNP with 0.45 ml of 10 mM Zwittergent 3-14 and 5.85 ml water and preincubation follows addition only of 0.9 ml of 1.0 M Tris-HCl (pH 8.0) and mixing. Reaction is carried out by adding to 0.8 ml of the preincubated substrate 0.1 ml phospholipase C preparation and 0.1 ml which is either 10 units of alkaline phosphatase in water or 0.1 ml of water, the combining being done in a quartz cuvette. The reaction mixture contains 0.1 M Tris-HCl (pH 8.0), 0.1 mM Zwittergent 3-14, 0.5 mM PpNP, none or 10 units of alkaline phosphatase per 1 ml and from 0 to 1 unit of phospholipase C per 1 ml (as phospholipase C hydrolyzes PpNP under these conditions at 37° C. at a rate which increases as a linear function of the phospholipase C concentration). The contents are mixed and the rate of p-nitrophenol appearance monitored continuously at 404 nm at 37° C. in a spectrophotometer equipped with a chart recorder.

PpNP is hydrolyzed by phospholipase C to diacylglycerol and p-nitrophenylphosphate which in turn is further hydrolyzed by an excess of alkaline phosphatase to inorganic phosphate and free p-nitrophenol.

The rate of phospholipase C catalyzed hydrolysis of PpNP is the difference between the hydrolytic rate measured when both the phospholipase C sample and alkaline phosphatase are present in the assay mixture and the reaction rate when the phospholipase C sample is present but the alkaline phosphatase is not. The hydrolytic rate measured with each phospholipase C sample without alkaline phosphatase represents phospholipse D catalyzed hydrolysis of that sample plus the change in absorbance at 404 nm of the substrate suspension under the conditions of the reaction. The alkaline phosphatase used in the assay has no activity toward intact PpNP.

For each sample, the absorbance at 404 nm is recorded as a function of time for a period of 15 minutes.

The determination of the rate of PpNP hydrolysis from the rate of change of absorbance at 404 nm is accomplished as in Example III but using $14.52 \times 10^3 M^{-1} cm^{-1}$ as the molar absorptivity coefficient for p-nitrophenol at pH 8.0. Subtracting the control rate from the total rate for each sample gives the phospholipase C catalyzed rate of hydrolysis of PpNP which is proportional to the amount of phospholipase C present in the sample and is therefore translatable into phospholipase C activity.

EXAMPLE V

Synthesis of 1,2-Dipalmitoyl phosphatidyl-α-Naphthol (PaN)

The synthesis of α-naphthylphosphorodichloridate is carried out by the method of Friedman, O.M., and Seligman, A.M., J. of the American Chemical Society (1950), 72, pp 624–625.

PaN is synthesized by reacting α-naphthylphosphorodichloridate with D(−)-1,2-dipalmitin as follows: To 20 ml of boiling, dry, diethylether, containing 1.8 mmoles of D(−)-1,2-dipalmitin, and 3.4 mmoles triethylamine is added, dropwise with stirring, 7 ml of dry, diethylether containing 2.3 mmoles of α-naphthylphosphorodichloridate. The disappearance of the D(−)-1,2-dipalmitin and the appearance of product is followed by TLC. When the D(−)-1,2-dipalmitin is maximally consumed, 1 ml of triethylamine and 0.2 ml of water are added to the reaction mixture which is then refluxed for 2 hours. The reaction mixture is then acidified with 10 ml of 1 N HCl and is then extracted three times with diethylether. The ether solution is then washed with water, dried over anhydrous $MgSO_4$, evaporated and the residue dried further under vacuum over $P_2O_5$. Purification is carried out by the general scheme set forth in Example I.

EXAMPLE VI

Assay of Phospholipase D Using 1,2-Dipalmitoyl phosphatidyl-α-naphthol (PaN)

The assay of phospholipase D from cabbage using PaN prepared as set forth in Example V as the substrate is carried out in the same manner as set forth in Example III where PpNP was used as a substrate but with specific modifications required for the quantitation of the α-naphthol released from PaN by phospholipase D. The same number of moles of PaN is used in this assay as the number of moles of PpNP in Example III ($2.4 \times 10^{-6}$ moles). There are no further modifications to the assay from the protocol cited in Example III until the point where the timed aliquots are added to the quench solution. The quench solution differs from that in Example III in that 150 mM sodium acetate (pH 5.0) is substituted for 150 mM glycine (pH 10.4) and an additional component, 0.2 mM fast red TR salt is included. The fast red TR salt (diazotized 2-amino-5-chlorotoluene) couples with the free α-naphthol, released from PaN by phospholipase D, forming the colored complex which is subsequently quantitated spectrophotometrically. The performance of the actual assay, the mechanics and the timing, are carried out the same as stated in Example III. The quantitation of the α-naphthol-fast red TR colored complex is carried out as in Example III with the modification of using 405 nm instead of 404 nm as the wavelength of light and using $12.9 \times 10^3 M^{-1} cm^{-1}$ as the molar absorptivity coefficient of the colored complex.

EXAMPLE VII

Assay of Phospholipase C Using PaN and Supplementary Enzyme

Phospholipase C is assayed using PcN as the substrate. PaN is hydrolyzed to diacylglycerol and α-naphthylphosphate by phospholipase C. The α-naphthylphosphate is subsequently hydrolyzed by acid phosphatase to free phosphate and α-naphthol, and the latter reacts with fast red TR salt to form a colored complex which is quantitated spectrophotometrically.

The assay is performed as in Example IV with exceptions as noted. The substrate suspension is prepared as in Example IV substituting PcN for PpNP. The preincubation is carried out as in Example IV substituting 0.9 ml of 1.0 M sodium acetate (pH 6.0) for the Tris-HCl. The measurement of the reaction rate is accomplished as set forth in Example IV with the exceptions of the requirement for fast red TR salt and exchanging acid phosphatase for alkaline phosphatase. The fast red TR salt solution is $0.2 \times 10^{-6}$ moles per 0.050 ml and the acid phosphatase solution is 10 units per 0.050 ml of water. The phospholipase C sample control consists of a 1 cm quartz cuvette containing 0.8 ml of the substrate suspension, 0.10 ml of the phospholipase C sample, 0.050 ml of the fast red TR solution and 0.050 ml of water whereas each phospholipase C assay cuvette contains 0.8 ml of the substrate suspension, 0.10 ml of the phospholipase C sample, 0.050 ml of the fast red TR solution and 0.050 ml containing 10 units of acid phosphatase. The measurement of the absorbance change is carried out as in Example IV except the wavelength used is 405 nm. The transformation of the data to moles per minute is accomplished as described in Example III using the molar absorptivity coefficient of $12.9 \times 10^3 M^{-1} cm^{-1}$

EXAMPLE VIII

Synthesis of 1,2-Dipalmitoyl phosphatidyl-4-methylumbelliferone (PMU)

Synthesis of 4-methylumbelliferonylphosphorodichloridate is carried out by the method of O.M. Friedman and A.M. Seligman, J. of the American Chemical Society (1950), Vol. 72, pp 624–625 except that an equivalent amount of 4-methylumbelliferone is substituted for the α-naphthol.

PMU is synthesized by reacting 4-methylumberiferonylphosphorodichloridate with D(−)-1,2-dipalmitin as follows: To 20 ml of boiling, dry, diethylether, containing 1.8 mmoles of D(−)-1,2-dipalmitin, and 3.4 mmoles triethylamine, is added, dropwise with stirring, 7 ml of dry, diethylether containing 2.3 mmoles of 4-methylumberiferonylphosphorodichloridate. The disappearance of the D(−)-1,2-palmitin and the appearance of product is followed by TLC. When the D(−)-1,2-dipalmitin is maximally consumed, 1 ml of triethylamine and 0.2 ml of water are added to the reaction mixture which is then refluxed for 2 hours. The reaction mixture is then acidified with 10 ml of 1 N HCl and is then extracted three times with diethylether. The ether solution is then washed with water, dried over anhydrous $MgSO_4$, evaporated, and the residue dried further under vacuum over $P_2O_5$. PMU is purified by preparative TLC in chloroform-methanol-water (70:26:4).

EXAMPLE IX

Assay of Phospholipase D Using 1,2-Dipalmitoyl phosphatidyl-4-methylumbelliferone (PMU) as a Substrate Phospholipase D from cabbage is assayed using PMU as the substrate. Phospholipase D hydrolyzes PMU at a rate which increases as a linear function of phospholipase D concentration under the same conditions as set forth in Example III.

The assay is performed the same as in Example III except for the substitution of $2.4 \times 10^{-6}$ moles of PMU for the $2.4 \times 10^{-6}$ moles of PpNP and except for the quantitation. The quantitation of the released 4-methylumbelliferone is accomplished spectrofluorometrically using a standard curve.

The standard curve is made up from spectrofluorometric measurements on standard solutions containing a range of concentrations of 4-methylumbelliferone.

The standard curve is constructed based on measurements on solutions made up as follows. The normal assay solution containing everything but the enzyme solution is supplemented with a range of known quantities of pure 4-methylumbelliferone contained in the same volume as that in which the enzyme solution would normally have been added (0.10 ml) and then aliquots are added to quench solution in the normal proportions to provide the standard solutions. This is carried out by making up a stock solution of 4-methylumbelliferone of 5 mM and using it to make up a plurality of different concentration solutions spanning the range of 5 to 0.05 mM 4-methylumbelliferone. These solutions are in turn used to make up the standard solutions by adding 0.10 ml of 4-methylumbelliferone containing solution to the normal volume of standard, preincubated assay mixture (0.90 ml) instead of the 0.10 ml of enzyme solution which is added in the normal course of an assay, and adding 0.10 ml of the combination to 0.9 ml of quenching solution. A solution is also made up this same way except that 0.10 ml water is used in place of 4-methylumbelliferone containing solution. The spectrofluorometer is set for 365 nm light for excitation and 465 nm emmision and the electronic zero is set using the preparation containing water instead of 4-methylumbelliferone. All readings are made using a quartz cuvette which is clear on all sides. The standard curve is constructed relating the number of moles of 4-methylumbelliferone in the 0.10 ml aliquots of the solutions added to the assay mixtures to the fluorescence intensity.

In carrying out the assay, readings are taken over time intervals as in Example III but the spectrofluorometric readings herein are in terms of fluorescence intensity and are translated to moles of 4-methylumbelliferone released with the aid of the standard curve. The number of moles released per minute is translated to units of phosphlipase D as in Example III.

EXAMPLE X

Assay of Phospholipase C Using PMU and Supplementary Enzyme

Phospholipase C is assayed using PMU as the substrate in the same manner as set forth in Example IV for PpNP with the exceptions of exchanging PMU in equimolar amounts for PpNP and quantitating spectrofluorometrically instead of spectrophotometrically. The measurement of the reaction rate is accomplished using a recording spectrofluorometer, temperature regulated to 37° C., continuously recording the fluorescense intensity, using 365 nm light for excitation and measuring the emission light at 465 nm as a function of time. The rate of the phospholipase C catalyzed hydrolysis is determined using the same approach set forth in Example IV. Translation of the rate of increase in fluorescent intensity to rate of PMU hydrolysis is made using standard curves which relate fluorescence intensity to moles of 4-methylumbelliferone released. The curves are constructed the same way as the curve of Example IX except that 0.8 ml assay mix is used instead of 0.9 ml for each standard solution and in the case of one curve 0.1 ml pure water is an additional ingredient for each standard solution and in the case of the other curve 0.1 ml containing 10 units alkaline phosphatase is an additional ingredient for each standard solution. The curve generated based on the samples containing alkaline phosphatase is used in determining total 4-methylumbelliferone release rate. The other curve is used in determining the 4-methylumbelliferone release attributable to phospholipase D and the change in fluorescence of the substrate suspension under the conditions of the reaction. As in Example IV measurements are made with and without alkaline phosphatase being present and the curves are used to translate the rates of fluorescent intensity to moles of 4-methylumbelliferone released per minute in each case with the difference being the number of moles released per minute due to phospholipase C which is proportional to the amount of phospholipase C present and is there translatable into phospholipase C activity.

While the foregoing describes preferred embodiments, modifications within the scope of the invention will be evident to those skilled in the art. Thus the scope of the invention is intended to be defined by the claims.

What is claimed is:

1. Diacylglycerophosphoric acid ester having the following structural formula:

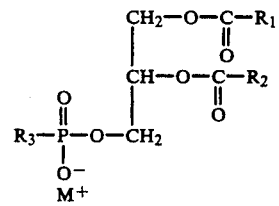

wherein $R_1$ $R_2$ are organic groups where at least one of them or the combination of them causes the compound to be insoluble in water, $R_3$ is a chromogenic head group which is released in enzymatic cleavage by phospholipase D from cabbage to form a chromophore or a molecule which reacts with diazotizing agent to form a chromophore and contains substituted phenol or naphthol or substituted naphthol of substituted umbelliferone and $M^+$ is a balancing cation.

2. Diacylglycerophosphoric acid ester as recited in claim 1 wherein $R_1$ and $R_2$ are independently selected from the group consisting of aliphatic, aryl and alkylaryl groups; and wherein when $R_1$ and $R_2$ are both aliphatic, each contains from 1 to 23 carbon atoms; and wherein the alkyl in any alkylaryl group contains from 1 to 17 carbon atoms.

3. Diacylglycerophosphoric acid ester as recited in claim 2 wherein $R_1$ and $R_2$ are aliphatic.

4. Diacylglycerophosphoric acid ester as recited in claim 3 wherein $R_1$ and $R_2$ are alkyl and each contains from 13 to 17 carbon atoms.

5. Diacylglycerophosphoric acid ester as recited in claim 4 wherein $R_3$ is p-nitrophenol.

6. Diacylglycerophosphoric acid ester as recited in claim 5 which is 1,2-dipalmitoyl phosphatidyl-p-nitrophenol.

7. Diacylglycerophosphoric acid ester as recited in claim 4 which is 1,2-dipalmitoyl phosphatidyl-α-naphthol.

8. Diacylglycerophosphoric acid ester as recited in claim 4 which is 1,2-dipalmitoyl.

* * * * *

UNITED STATES PATENT AND TRADEMARK OFFICE
CERTIFICATE OF CORRECTION

PATENT NO. : 5,011,964

DATED : April 30, 1991

INVENTOR(S) : Dennis C. Mynarcik et al

It is certified that error appears in the above-identified patent and that said Letters Patent is hereby corrected as shown below:

On the cover page under "[22] Filed: April 6, 1990", insert --Related U.S. Application Data

[63] Continuation of Ser. No. 709,256, Mar. 7, 1985, abandoned--.

Claim 8 (column 18, line 7), after "dipalitoyl" insert --phosphatidyl-4-methylumbelliferone--

Signed and Sealed this

Twenty-fifth Day of August, 1992

Attest:

DOUGLAS B. COMER

Attesting Officer

Acting Commissioner of Patents and Trademarks